US 8,252,150 B1

(12) United States Patent
Hsu et al.

(10) Patent No.: US 8,252,150 B1
(45) Date of Patent: Aug. 28, 2012

(54) EXTRACTIVE DISTILLATION PROCESS FOR RECOVERING BUTADIENE FROM $C_4$ HYDROCARBON MIXTURES

(75) Inventors: Kaochih Hsu, Katy, TX (US); Kuiwu Li, Beijing (CN)

(73) Assignee: International Innotech Inc., Katy, TX (US)

( * ) Notice: Subject to any disclaimer, the term of this patent is extended or adjusted under 35 U.S.C. 154(b) by 0 days.

(21) Appl. No.: 13/089,682

(22) Filed: Apr. 19, 2011

(51) Int. Cl.
*B01D 3/34* (2006.01)
(52) U.S. Cl. ............. 203/50; 203/53; 585/326; 585/810
(58) Field of Classification Search .................... 203/50, 203/53; 585/810, 326
See application file for complete search history.

(56) References Cited

U.S. PATENT DOCUMENTS

| | | | |
|---|---|---|---|
| 2,386,310 A * | 10/1945 | Hachmuth | 585/314 |
| 3,541,178 A | 11/1970 | Nettesheim | |
| 3,842,137 A | 10/1974 | Dickinson | |
| 3,898,298 A | 8/1975 | Desiderio | |
| 4,038,156 A * | 7/1977 | Knott et al. | 203/45 |
| 4,128,457 A | 12/1978 | Barba et al. | |
| 4,277,313 A | 7/1981 | Mehra | |
| 4,469,907 A | 9/1984 | Araki et al. | |
| 4,704,492 A | 11/1987 | Nemet-Mavrodin | |
| 5,414,170 A | 5/1995 | McCue et al. | |
| 6,040,489 A | 3/2000 | Imai | |
| 7,393,992 B2 | 7/2008 | Hill et al. | |
| 2002/0052533 A1 * | 5/2002 | Koga et al. | 585/313 |
| 2006/0235257 A1 * | 10/2006 | Bridges et al. | 585/810 |
| 2009/0105514 A1 * | 4/2009 | Lee et al. | 585/808 |

FOREIGN PATENT DOCUMENTS

CN 101838177 A 9/2010

OTHER PUBLICATIONS

Buell, C., Boatright, R., "Furfural Extractive Distillation", Industrial and Engineering Chemistry, vol. 39 No. 6, American Chemical Society (c) 1947.*
Davis, G., Makin, E., Middlebrooks, C., "Process Evaluation of Improved Solvents for Butadiene Recovery", Advances in Chemistry, American Chemical Society (c) 1970.*
Chen, F., Zheng J., "Operation Parameters Optimization of Butadiene Extraction Distillation Based on Neural Network", Proceedings of the 2011 6th IEEE Interarntional Conference on nano/micro Engineered and Molecular Systems, Feb. 2011.*
W.C. White, "Butadiene Production Process Overview" Chemico-Biological Interactions, 166 (2007) 10-14.

* cited by examiner

*Primary Examiner* — Robert A Hopkins
(74) *Attorney, Agent, or Firm* — Cascio & Zervas

(57) ABSTRACT

High purity 1,3 butadiene is recovered from a $C_4$ fraction containing butadienes, butenes, butanes, and acetylenes that is generated from a steam cracker by extractive distillation operating with no reflux or greatly reduced reflux conditions. This no reflux (or minimum reflux) technique is generally applicable to any butadiene recovery process in which at least one extractive distillation column (EDC) is used to separate 1,3 butadiene from other $C_4$ components in the mixture. For an ED process with two EDCs, significant reductions in total energy requirements in the both EDCs can be achieved by appropriate reductions in the reflux in each column. The performances of both EDCs are unaffected even when operating at no reflux.

19 Claims, 3 Drawing Sheets

EXTRACTIVE DISTILLATION PROCESS FOR RECOVERING BUTADIENE FROM $C_4$ HYDROCARBON MIXTURES

FIELD OF THE INVENTION

The present invention is directed to extractive distillation processes for recovering high purity 1,3 butadiene from $C_4$ fractions that are generated in a steam cracker and which contain butadienes, butenes, butanes, and acetylenes. The extractive distillation column(s) are operated with no reflux (or at significantly reduced reflux levels) which unexpectedly enhances energy and throughput efficiency of the extractive distillation columns without compromising their performance.

BACKGROUND OF THE INVENTION

Butadiene is normally produced during the pyrolysis of petroleum fractions. For example, producing ethylene and propylene by pyrolysis of petroleum gas, naphtha, or gas oil in a steam cracker also yields secondary products that include significant amounts of a $C_4$ hydrocarbon fraction that is rich in 1,3 butadiene and butenes and has minor amounts of acetylenes. Conventional distillation however cannot separate 1,3 butadiene with the required purity from this $C_4$ hydrocarbon fraction due to the closeness of boiling points and, thus, small differences in the relative volatilities of the components.

Extractive distillation (ED) has long been the only method of choice for recovering high purity 1,3 butadiene from the close-boiling $C_4$ hydrocarbon mixture. This method entails adding a selective solvent (also referred to as an extractant), which has a boiling point that is significantly higher than that of the $C_4$ mixture, to the distillation column to increase the differences in the relative volatilities of the components to be separated from one another. A single extractive distillation column (EDC) however yields only crude butadiene that contains acetylenes, which are deleterious to the polymerization of 1,3 butadiene, and other troublesome impurities.

There are two primary approaches for subsequently removing the major impurities from the crude butadiene: (1) selective hydrogenation of the acetylenes in a separate reactor or column and (2) selective removal of the acetylenes in a second EDC followed by additional distillations, where necessary. Both strategies for removing acetylene impurities require crude butadiene production with an initial EDC. Examples of the selective hydrogenation approach are disclosed U.S. Pat. No. 3,541,178 to Nettesheim, U.S. Pat. No. 3,842,137 to Dickenson, U.S. Pat. No. 3,898,298 to Desiderio et al., U.S. Pat. No. 4,277,313 to Mehra, U.S. Pat. No. 4,469,907 to Araki et al., U.S. Pat. No. 4,704,492 to Nemet-Mavrodin, U.S. Pat. No. 5,414,170 to McCue et al., U.S. Pat. No. 6,040,489 to Imai and U.S. Pat. No. 7,393,992 to Hill et al. A technique embodying the second approach is described in U.S. Pat. No. 4,128,457 to Barba et al. whereby a second EDC using aqueous acetonitrile as the selective solvent and downstream distillation columns are employed to remove the acetylenes. The second EDC represents a major capital investment and another energy intensive operation.

Instead of using a second EDC for acetylenes removal, U.S. Pat. No. 4,038,156 to Knott et al. describes a process configuration that features flashing a rich solvent containing 1,3 butadiene, acetylenes and minor amounts of $C_5$ hydrocarbons from the bottom of an EDC into a flash drum and feeding a liquid stream from the flash drum to a first stripping column where acetylenes are removed from a side-cut, lean solvent is removed from the bottom for recycling to the EDC, and vapor containing 1,3 butadiene, traces of $C_5$ and the solvent is removed from the top. A mixed vapor stream from the top of the first stripping column and from the flash drum is compressed and most of the compressed vapor is fed to a second stripping column to recover purified 1,3 butadiene. The overall process is also capital and energy intensive since it requires an EDC, two distillation columns (one for water separation), two water wash columns, and two stripping columns.

Solvent capability limitations restrict the degree to which the number and size of separation trays in an EDC can be reduced and still recover high purity 1,3 butadiene from $C_4$ fractions. The art is in need of minimizing utilities or energy consumption while enhancing the throughput of existing EDCs without major equipment revamping and capital expenditures.

SUMMARY OF THE INVENTION

Extractive distillation is a preferred method for recovering high purity 1,3 butadiene from the close-boiling $C_4$ hydrocarbon mixture generated in a steam cracker. The present invention includes novel methods of operating the extractive distillation column (EDC) in different ED process configurations with substantially reduced utilities and energy consumption. The invention also provides techniques for modifying existing 1,3 butadiene recovery processes where the EDC is the bottleneck to enhance throughput without any major equipment modifications or capital expenditures.

The present invention is based in part on the recognition that reducing the reflux ratio of the EDC has essentially no detrimental effect on the column's performance in separating 1,3 butadiene from $C_4$ hydrocarbon mixtures.

Accordingly, in one aspect the invention is directed to an extractive distillation process, that employs first and second extractive distillation columns (EDCs) for recovering high purity 1,3 butadiene from $C_4$ hydrocarbon fractions that includes the steps of:

(a) introducing a $C_4$ hydrocarbon feed mixture containing 1,3 butadiene into a middle portion of a first EDC and introducing a first solvent-rich stream into an upper portion of the first EDC as a first selective solvent feed;

(b) recovering a first raffinate stream rich in less polar hydrocarbon components from a top of the first EDC, that is substantially free of 1,3 butadiene and the first selective solvent, and withdrawing a second solvent-rich stream containing the first selective solvent and more polar components from a bottom of the first EDC;

(c) introducing the second solvent-rich stream into a middle portion of a first stripping column (SC), recovering a more polar hydrocarbon-rich stream from a top of the SC, which is then fed to a compressor to yield a compressed stream, and removing a third solvent-rich stream from a bottom of that SC, that is recycled to the upper portion of the first EDC as the first selective solvent feed;

(d) introducing the compressed stream in step (c) into a middle portion of a second EDC and introducing a fourth solvent-rich stream into an upper portion of the second EDC as a second selective solvent feed;

(e) recovering a second raffinate stream containing essentially 1,3 butadiene with minor amounts of butenes, traces of acetylenes, and substantially free of the second selective solvent from a top of the second EDC, and withdrawing a fifth solvent-rich stream from a bottom of the second EDC;

(f) introducing the fifth solvent-rich stream into a middle portion of a second stripping column (SC), removing a stream rich in vinylacetylene from a top of the second SC, which is preferably purged as fuel, and recovering a sixth solvent-rich stream from a bottom of the second SC, that is recycled to the upper portion of the second EDC as the second selective solvent feed;

(g) introducing the second raffinate stream from step (e) into a middle portion of an acetylene fractionator, removing a small stream rich in 1,3 butadiene and methylacetylene from a top, which is preferably purged as fuel, and recovering a crude 1,3 butadiene stream from a bottom of the fractionator; and (h) introducing the crude 1,3 butadiene stream from step (g) into a middle portion of a butadiene fractionator, where the purified 1,3 butadiene is recovered from an overhead and minor amounts of impurities are preferably purged from a bottom of the fractionator as fuel.

In this ED process with the pair of EDCs, it is expected that a saving of over 40% in the total energy requirements of the first EDC can be achieved by operating the first EDC with 95% reduction in the reflux, for example, at a reflux ratio of 0.1 to 0.05. A savings of over 35% can be achieved for the second EDC when that latter is operated at 73% reduction in the reflux for example, at a reflux of ratio of 0.2 to 0.4. The performances of the two EDCs are not affected even when operating under a reflux ratio in the range of 0 to 0.05 (a reduction of 98 to 100% (no reflux)).

In order to prevent solvent entrainment in the overhead raffinate product of the first EDC, the solvent feed tray is preferably moved downward away from the top of the first EDC. However, entrained solvent may still be detected in the overhead raffinate product under no reflux operations, but this can be easily remedied by adding as little as 5% of the original reflux to the first EDC (a 95% reduction). Water wash to remove the entrained solvent from the raffinate stream is a preferred option for the first EDC when using an aqueous selective solvent, such as aqueous ACN, aqueous NMP. In this fashion, the first EDC can operate under no reflux conditions and without having to lower the location of the lean solvent feed tray.

For the second EDC, on the other hand, entrained solvent in the raffinate stream should not be a problem because it can be readily removed in the down-stream distillation columns that are configured to purify the 1,3 butadiene product. Therefore, the second EDC can operate with no reflux without having to lower the lean solvent feed tray location. Operation of the first EDC requires three times the energy that is needed by the second EDC so more savings can be realized by efficient operations of the first EDC.

The no reflux (or minimum reflux) concept with respect to the EDC can be applied broadly to any butadiene recovery process in which at least one EDC, but preferably only a single EDC, is used to separate 1,3 butadiene from a mixture containing it and other $C_4$ components. For example, the invention is particularly suited for extension into processes in which hydrogenation is used to eliminate acetylenes in a feed mixture. In these applications, typically only one EDC is required to produce highly pure 1,3 butadiene. The single EDC is thus the critical unit for improvement.

Accordingly, another aspect of the invention is directed to an ED process that uses aqueous selective solvents for recovering high purity 1,3 butadiene from $C_4$ hydrocarbon fractions, which includes the steps of:

(a) introducing a $C_4$ hydrocarbon feed mixture containing 1,3 butadiene into a middle portion of an EDC and introducing a first solvent-rich stream into an upper portion of the EDC as a selective solvent feed;

(b) recovering a first raffinate stream rich in less polar hydrocarbon components from a top of the EDC, that is substantially free of 1,3 butadiene, and withdrawing a second solvent-rich stream containing the selective solvent and more polar components from a bottom of the EDC;

(c) introducing the second solvent-rich stream into a flash drum and recovering butadiene-rich vapor in a top of the flash drum and recovering rich solvent that is partially depleted of butadiene in a bottom of the flash drum;

(d) introducing the rich solvent recovered in step (c) to an upper portion of a first stripping column, introducing lean solvent from a bottom of the second stripping into the upper portion of the first stripping column to recover hydrocarbons remaining in the lean solvent, withdrawing a stream rich in acetylenes from a side-cut of the first stripping column for proper disposal, recovering a butadiene-rich vapor containing heavier impurities from the top of the first stripping column, and recovering the lean solvent from the bottom of first stripping column, which is recycled back to the upper portion of the EDC in step (a);

(e) combining the butadiene-rich vapor stream from the top of the first stripping column in step (d) and the butadiene-rich vapor stream from the top of the flash drum to form a combined mixture rich in 1,3 butadiene that is fed to a compressor;

(f) splitting the compressed vapor from step (e) into three portions: (i) a first major portion (typically comprising between 30 to 50% of the vapor) for recycling to the lower portion of the EDC for improving its operation; (ii) a second major portion (typically comprising between 30 to 50% of the vapor) for recycling to middle portion of the second stripping column for recovering purified 1,3 butadiene product; and (iii) a minor portion (typically comprising between 5 to 15% of the vapor) to a water wash section for removing and recovering $C_5$ hydrocarbons; and (g) introducing the raffinate stream from step (b) to the water wash of section (0 to remove entrained solvent from the raffinate product.

DETAILED DESCRIPTION OF THE PREFERRED EMBODIMENTS

The present invention is based in part on the recognition that incorporating reflux in an EDC for separating 1,3 butadiene from $C_4$ hydrocarbon mixtures does not enhance the performance of the EDC. The reflux in the EDC essentially serves only to knock down entrained solvent in the overhead raffinate product. Elimination of the EDC reflux can substantially reduce the steam consumption in the bottom reboiler, minimize the cooling duty of the overhead condenser, and decrease the vapor loading of the upper portion of the column, thereby, increasing the column's throughput.

In a conventional distillation column, the overhead liquid reflux generates the liquid phase in the rectifying section of the column which contacts the uprising vapor phase from tray-to-tray as the key components in a feed mixture are separated. Depending on the application, the normal reflux-to-distillate ratio in a distillation column is approximately 1 to 20. In the EDC, however, the liquid phase in the rectifying section consists mostly of the nonvolatile, selective solvent that preferentially absorbs the more-polar components from the uprising vapor phase and allows the less-polar component vapors to ascend to the top of the ED column. Although it helps to knock down entrained solvent from the overhead raffinate stream, adding reflux to the EDC does not create the rectifying effect of distillation. Instead, the reflux tends to load up the capacity of the solvent and the capacity of the upper EDC. As a result, in both scenarios, energy is consumed simply to re-evaporate the reflux stream from the EDC. This can be particularly non-productive especially when the conventional first EDC and second EDC are operated under reflux ratio as high as 1 to 3. Moreover, the reflux also causes an increase in the solvent feed rate to the EDC by occupying the solvent capacity and reduces EDC throughput since the distillation capacity is dictated by the vapor loading which is significantly influenced by the reflux.

The present invention provides novel methods of operating the first EDC and the second EDC (if required) under reduced or no reflux conditions for 1,3 butadiene recovery from $C_4$ hydrocarbon fractions. The improved extractive distillation processes achieve substantial reductions in energy consumption with the original throughput. Alternatively, the improved process can increase the throughput of the EDC without necessitating any major equipment revamping.

Figure 1:
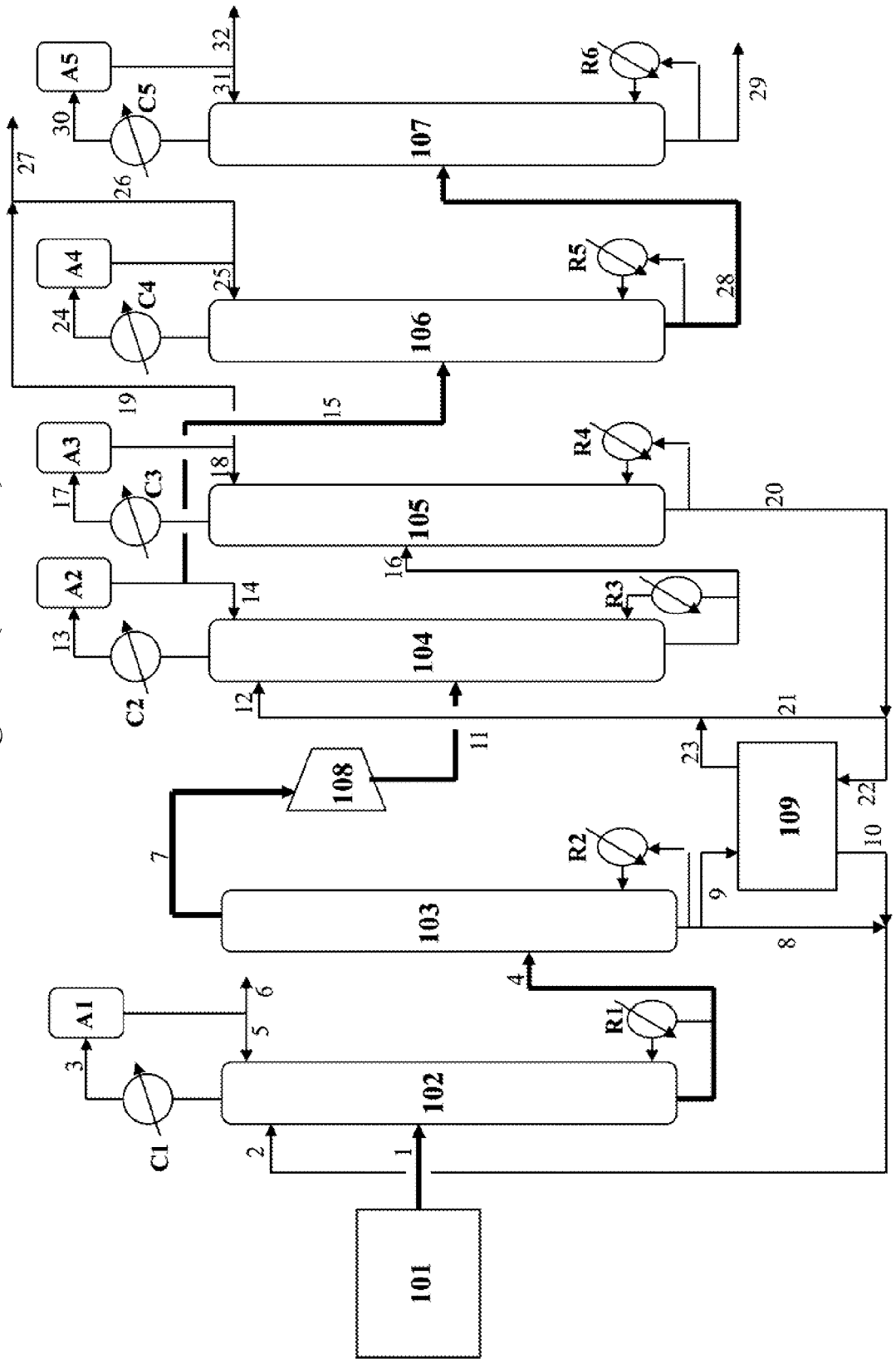
FIG. 1 is a schematic diagram of a commercial ED process with two EDCs for 1,3 butadiene recovery from $C_4$ hydrocarbon fractions wherein both EDCs are illustrated as operating with reflux.

Referring to FIG. 1, a crude $C_4$ fraction containing 1,3 butadiene from tank 101 is fed to the middle portion of a first EDC 102 via line 1, while a lean solvent is introduced into the upper portion of EDC 102 through line 2. Through line 3, an overhead vapor stream containing mainly of butenes is condensed by cooler C1 before entering accumulator A1, from which a larger portion of the condensate is recycled back to EDC 102 via line 5 as the reflux (with a reflux ratio of normally 2 to 3), while the balance is withdrawn from the top of EDC 102 via line 6 as the $C_4$ raffinate product. A rich solvent stream containing butadienes, acetylenes, and solvent is transferred from the bottom of EDC 102 to a first stripping column 103 via line 4 where 1,3 butadiene and acetylenes are stripped as vapor from the solvent and recovered at the top of column 103 via line 7; the vapor is then fed to compressor 108. A portion of the rich solvent is heated in reboiler R1 and recycled to the bottom of EDC 102 to supply the heat for the column.

Lean solvent that is withdrawn from the bottom of column 103 is recycled to EDC 102 via lines 8 and 2. Similarly, a portion of the rich solvent is recycled through reboiler R2 to the bottom of column 103 to supply the heat for the column. A slip stream of the lean solvent is fed to a solvent purification unit 109 via line 9 for regeneration, and the regenerated lean solvent is recycled via line 10 and mixed with lean solvent in line 8. A compressed vapor stream from compressor 108 is fed to the middle portion of the second EDC 104 via line 11, while the lean solvent is introduced into the upper portion of EDC 104 through line 12. An overhead stream containing mainly 1,3 butadiene, small amounts of cis-2-butene, and traces of methylacetylene is condensed in cooler C2 before entering accumulator A2 via line 13, from which a larger portion of the condensate is recycled back to EDC 104 as reflux via line 14 (with reflux ratio normally >1.0), while the balance is withdrawn and fed into an acetylene fractionator 106 via line 15; rich solvent comprising vinylacetylene, minor amounts of heavier impurities, and solvent is removed from the bottom of EDC 104 and transferred to the second stripping column 105 via line 16 where vinylacetylene and the heavier impurities are stripped and condensed in cooler C3 and transferred to accumulator A3 in the overhead of column 105 via line 17. A portion of the condensate is recycled back to column 105 as reflux through line 18, while the balance is withdrawn from the top of column 105 via lines 19 and 27 to be purged as fuel. Lean solvent withdrawn from the bottom of column 105 is recycled to EDC 104 via lines 20, 21 and 12. A slip stream of the lean solvent is fed to solvent purification unit 109 via line 22 for regeneration, and the regenerated lean solvent is recycled via line 23 mixed with lean solvent in line 21

A stream in line 15 containing mainly 1,3 butadiene with minor amounts of methylacetylene and impurities is fed to acetylene fractionator 106 to remove methylacetylene from the overhead through cooler C4 and accumulator A4 via line 24. A portion of the condensate is recycled back to column 106 as reflux through line 25 and the other portion is purged through lines 26 and 27 as fuel. 1,3 butadiene and heavier impurities are transferred from the bottom of column 106 and fed to the butadiene fractionator 107 via line 28. Through line 30, vapor consisting of purified 1,3 butadiene withdrawn from the overhead is condensed through cooler C5 before entering accumulator A5 where a portion of the condensate is recycled to column 107 as reflux via line 31, and the balance is recovered as purified 1,3 butadiene through line 32. Heavier impurities are purged as fuel from the bottom of column 107 via line 29. A portion of the bottom stream from each of columns 104, 105, 106 and 107 are recycled through their associated reboilers R3, R4, R5 and R6, respectively, to heat each column.

Figure 2:
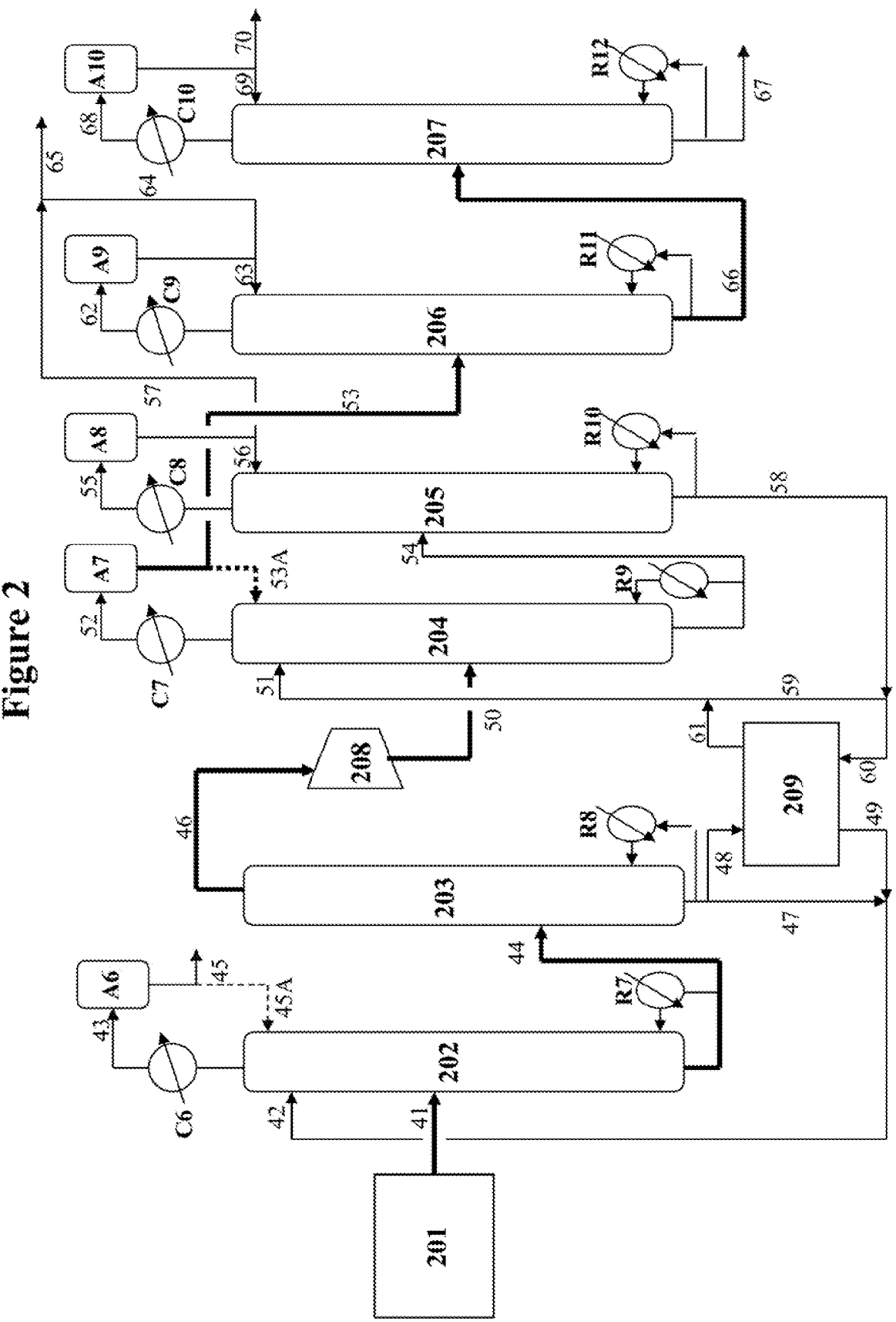
FIG. 2 is a schematic diagram of a commercial ED process with two EDCs for 1,3 butadiene recovery from $C_4$ hydrocarbon fractions wherein both EDCs are illustrated as operating without reflux or greatly reduced reflux.

FIG. 2 illustrates an improved extraction distillation process in which the first and the second ED columns are operated under no reflux or greatly diminished reflux. The performances of both EDCs are not significantly adversely affected with respect to producing high purity butadiene product as compared to the process shown in FIG. 1. As an example, with non-aqueous DMF as the selective solvent, the reduction in energy consumption is substantial: more than 40% in the first EDC and more than 35% in the second EDC with minimal capital investment and process modification.

As shown in FIG. 2, a crude $C_4$ fraction containing butadiene from tank 201 is fed to the middle portion of the first EDC 202 via line 41, while a lean solvent is introduced into the upper portion of EDC 202 through line 42. The fraction includes, among other hydrocarbons, the more polar hydrocarbons such as butadienes, including 1,3 butadiene and 1,2 butadiene, and acetylenes, including methylacetylene, ethylacetylene and vinylacetylene, and the less polar hydrocarbons such as butanes and butenes including 1-butene, isobutene, and 2-butenes.

Through line 43, an overhead vapor stream containing mainly the butenes is condensed by cooler C6 before entering accumulator A6, from which the condensate is withdrawn as the $C_4$ raffinate product via line 45. In a preferred embodiment, no condensate or only a minimal amount is recycled via line 45A to first EDC 202 as reflux, since it does not enhance the separation, other than in helping knock down entrained solvent from the raffinate product. The reflux can be reduced from 40% to up to 98% to 100% of the original amount, more preferably, by 80 to 100%, and most preferably by 95 to 100%. In other words, the reflux ratio can be 0 (no reflux) to 1.08, more preferably 0 to 0.36, and most preferably 0 to 0.18. First EDC 202 preferably comprises 150 to 250 trays and second EDC 204 preferably comprises 60 to 120 trays.

To prevent solvent entrainment in the raffinate product, the lean solvent entry point can be moved to a lower point in the column, preferably at 12 to 60 trays below the top of the column, and more preferably 25 to 45 trays below. That is the solvent entry is lowered to tray number 12 to 60, as measured from the top of the column. Similarly, the hydrocarbon feed entry point can be adjusted as necessary to maintain EDC 202 performance. Typically, the hydrocarbon feed enters through an entry point of first EDC 202 that is adjusted downward (from the top of the column) at trays 110 to 180 to maintain the performance of first EDC. That is the feed entry point is lowered to tray number 110 to 180, as measured from the top.

As further shown in FIG. 2, overhead vapor from column 203 is fed to compressor 208 via line 46 and the compressed vapor stream from compressor 208 is fed to the middle portion of the second EDC 204 via line 50, while the lean solvent is introduced into the upper portion of second EDC 204 through line 51. Through line 52, the overhead stream containing mainly 1,3 butadiene, small amounts of cis-2-butane, and traces of methylacetylene is condensed in cooler C7 before entering accumulator A7, from which the condensate is withdrawn as the crude butadiene via line 53. Again, no condensate or only a minimum amount of condensate is recycled to EDC 204 as the reflux via line 53A. The reflux can be reduced from 40% to up to 98% to 100% of the original amount, more preferably, by 70 to 100%, and most preferably by 80 to 100%. In other words, the reflux ratio can be 0 (no reflux) to 0.66, more preferably 0 to 0.33, and most preferably 0 to 0.18. Since the crude butadiene will be distilled twice in distillation columns 206 and 207, the entrained solvent can be easily removed from the purified butadiene product. The arrangement of the solvent trays in second EDC 204 does not need to be changed. The other portion of the condensate is transferred via line 53 to the acetylene fractionator 206. Impurities can be substantially removed in butadiene fractionator 207. It is understood that the extractive distillation process can be operated under various conditions including different reflux ratios depending on the particular parameter(s), such as energy savings and throughout, that is used for optimization. For example, when using non-aqueous DMF as the selective solvent, simulation results show that the process was optimized with respect to energy savings when employing a reflux ratio of 0.11 for the first EDC 202 and a reflux ratio of 0.3 for the second EDC 204. In one embodiment where the selective solvent is aqueous, such as aqueous NMP or aqueous ACN, the first EDC 202 can operate with no reflux, that is, with a reflux ratio of zero. The reflux ratio of the second EDC 204, which is less critical, can be about 0.1.

Rich solvent is transferred from the bottom of first EDC 202 and fed to the first stripping column 203 via line 44. Rich solvent withdrawn from the bottom of second EDC 204 is then fed to the second stripping column 205 via line 54. The stripped acetylene mixture is removed from the overhead of column 205 via line 55, which is condensed through cooler C8 and collected in accumulator A8. A portion of the condensate is recycled as the reflux via line 56 and the other portion is purged as fuel via lines 57 and 65. Lean solvent from the bottom of column 205 is recycled to second EDC 204 through lines 58, 59, and 51. A slip stream is withdrawn from line 58 and fed to solvent purification unit 209 via line 60 for solvent regeneration for regeneration, and the regenerated lean solvent is recycled via line 61 mixed with lean solvent in line 59.

The overhead from column 206 is condensed in cooler C9 and collected in accumulator A9 through line 62, from which a portion of the condensate is recycled as the reflux via line 63 and the other portion is removed via line 64 and combined with line 57 and the combined mixture is purged through line 65. The bottom stream from column 206 is transferred via line 66 to feed the butadiene fractionator 207. Purified butadiene exiting the top of column 207 via line 68 is condensed in cooler C10 and collected in accumulator A10, from which a portion is recycled as reflux via line 69 and the balance is withdrawn through line 70 as the purified butadiene product that is free of acetylenes. The bottom of column 207 is purged via line 67 as fuel.

A portion of the rich solvent is heated in reboiler R7 and recycled to the bottom of first EDC 202 to supply the heat for the column. Lean solvent that is withdrawn from the bottom of column 203 is recycled to EDC 202 via lines 47 and 42. Similarly, a portion of the lean solvent is recycled through reboiler R8 to the bottom of column 203 to supply the heat for the column. A slip stream of the lean solvent is fed to a solvent purification unit 209 via line 48 for regeneration, and the regenerated lean solvent is recycled via line 49 mixed with line 47. A portion of the bottom stream from each of columns 204, 205, 206 and 207 are recycled through their associated reboilers R9, R10, R11 and R12, respectively, to heat each column.

For the extractive distillation process illustrated in FIG. 2, the selective solvent include, for example, dimethylformamide (DMF), acetonitrile (ACN), N-methyl-pyrrolidone (NMP), dimethylacetamide (DMAC), furfural, phenol, sulfolane, methylethylketone (MEK), and mixtures thereof. Water can be included as a co-solvent.

The embodiment depicted in FIG. 2 is especially suited for non-aqueous solvents, such as DMF, where entrained solvent in the EDC overhead raffinate stream is not present. Water washing to remove entrained solvent from the raffinate is not an option since the entire process is water-free when a non-aqueous solvent is used. On the other hand, in the case where the ED process uses aqueous solvents, such as aqueous ACN, aqueous NMP, and aqueous methoxyproprionitrile/furfural, the entrained solvent in the raffinate from the ED column operated under no reflux or greatly diminished reflux, can be washed with water in a separated water wash tank or column. Under this condition, the solvent tray in the first ED column should not be changed.

Figure 3:
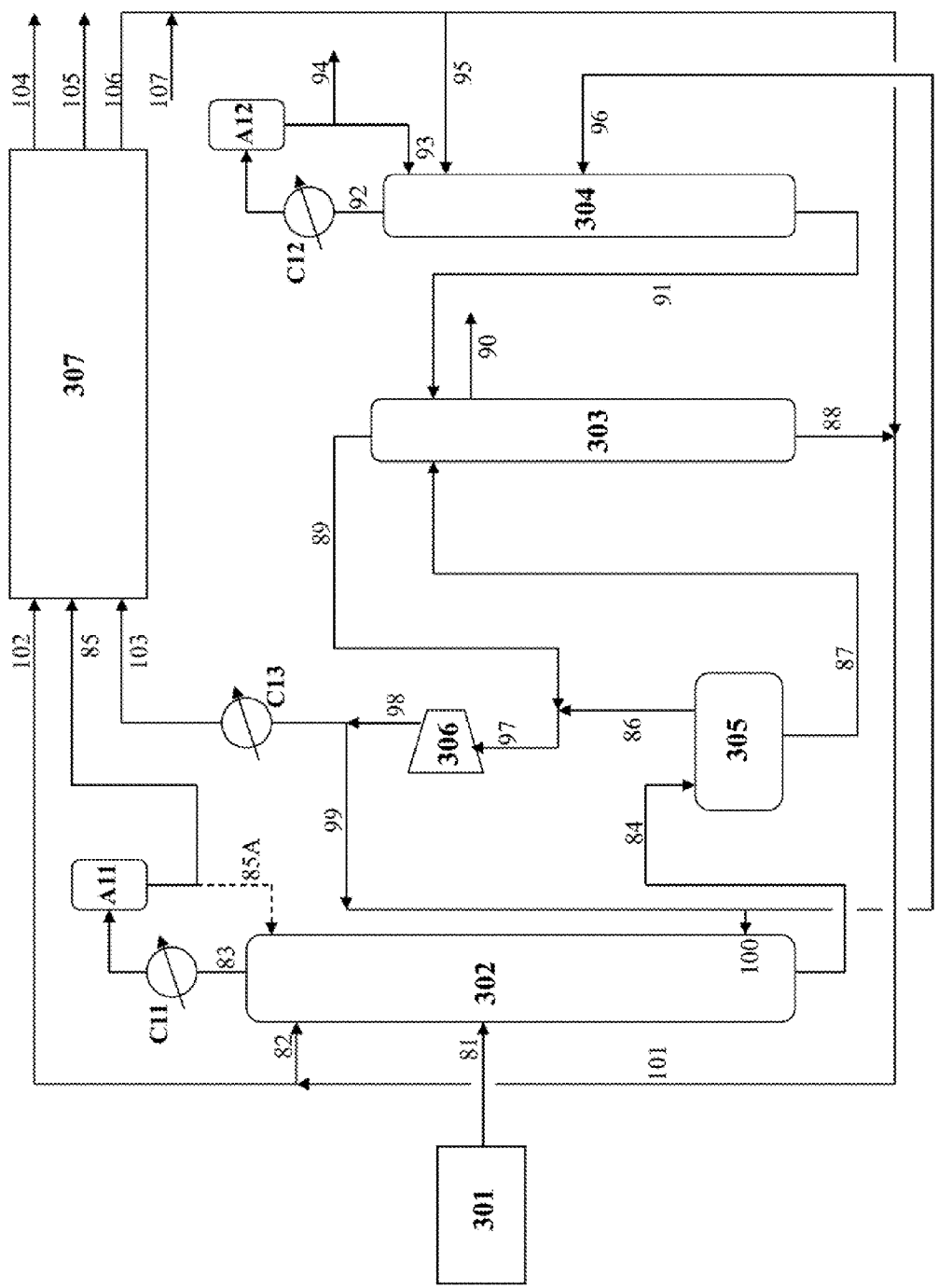
FIG. 3 is a schematic diagram of a commercial ED process with one EDC and a water wash section for 1,3 butadiene recovery from $C_4$ hydrocarbon fractions wherein the EDC is illustrated as operating without reflux.

One of the benefits of the present invention is that the no reflux or reduced reflux concept for the ED column can be applied to upgrade existing butadiene recovery processes in which at least one EDC is used to separate 1,3 butadiene from other $C_4$ components in a mixture. For example, U.S. Pat. No. 4,038,156 describes a butadiene recovery process consisting of a single EDC using aqueous ACN as the solvent, two stripping columns, and one flash drum, and a major water wash section for washing the raffinate product from the EDC and for recovering the lean solvent and water. FIG. 3 depicts the improvement of the system shown in U.S. Pat. No. 4,038, 156.

As illustrated in FIG. 3, a crude $C_4$ fraction containing 1,3 butadiene from tank 301 is fed to the middle portion of EDC 302 via line 81, while a lean solvent is introduced into the upper portion of EDC 302 through line 82. The fraction includes, among other hydrocarbons, more polar hydrocarbons such as butadienes, including 1,3 butadiene and 1,2 butadiene, and acetylenes, including methylacetylene, ethylacetylene and vinylacetylene, and less polar hydrocarbons are the butanes and butanes, including 1-butene, isobutene, and 2-butenes.

Through line 83, an overhead vapor stream containing mainly the butenes is condensed in cooler C11 before entering accumulator A11, from which the condensate is withdrawn from the top of EDC 302 as $C_4$ raffinate stream that is transferred to a water wash section 307 to remove the entrained solvent via line 85. No reflux or only a minimal reflux is recycled to EDC 302 via line 85A. The reflux can be reduced from 40% to up to 98% to 100% of the original amount, more preferably, by 80 to 100%, and most preferably by 95 to 100%. In other words, the reflux ratio can be 0 (no reflux) to 1.08, more preferably 0 to 0.36, and most preferably 0 to 0.18. The thermal energy required for the extractive distillation is supplied by the butadiene-rich vapor that is introduced via line 100 into the bottom of EDC 302. A rich solvent stream containing butadienes, acetylenes, and the solvent is transferred via line 84 from the bottom of EDC 302 to flash drum 305. The butadiene-rich vapor that is collected from the top of flash drum 305 is carried by lines 86 and 97 to compressor 306. Rich solvent partially depleted of butadiene is collected in the bottom of flash drum 305 and carried by line 87 to an upper portion of first stripping column 303. A butadiene-rich vapor containing some heavier impurities is recovered as an overhead product of column 303 via line 89 to the suction of compressor 306 where it is combined with the butadiene rich vapor from flash drum 305 in line 97.

Lean solvent exiting the bottom of first stripping column 303 is recycled back to EDC 302 via lines 88, 101, and 82. To maintain quality of the lean solvent, approximately 1% of the recycled lean solvent is fed to the water wash section 307 for regeneration via line 102. A solvent-rich stream rich in acetylenes is withdrawn from a side-cut of column 303 through line 90. The compressed vapor stream from compressor 306 transferred through line 98 is divided into three portions. The bulk of the stream is split between lines 96 and 100 for recycle to the bottom of the EDC 302 and to middle portion of the second stripping column 304, respectively. The remainder of the compressed vapor (less than 10%) is partially condensed in cooler C13 and fed to the water wash section 307 via line 103 for recovering the $C_5$ hydrocarbons, butadienes, and solvent. This water wash section, which is configured with two water wash columns and one distillation column, produces solvent-free raffinate stream through line 104, $C_5$ hydrocarbons through line 105, and lean solvent stream through line 106. Make up lean solvent is supplied through line 107.

Through line 92, vapor of purified 1,3 butadiene from the overhead of second stripping column 304 is condensed through cooler C12 and collected in accumulator A12, where a portion of the condensate is recycled back to column 304 as reflux via line 93 and the other portion is withdrawn as the purified 1,3 butadiene product via line 94. Lean solvent split off from the lean solvent recycle line 106 is injected via line 95 near the top of column 304 to facilitate the separation of acetylenic materials from the 1,3 butadiene product. Lean solvent withdrawn from the bottom of column 304 is recycled to the upper portion of first stripping column 303 through line 91 to recover any remaining hydrocarbons.

Since the raffinate stream in line 85 from the overhead of EDC 302 is water washed and distilled through water wash section 307 to remove the entrained solvent, the level of reflux can regulated by simply turning off a valve on the reflux line 85A. By operating under no-reflux or minimum reflux, a substantial energy saving in EDC 302 can be realized. Other systems where the invention can be applied include processes in which hydrogenation is used to eliminate the acetylenes in the feed mixture in which only a single EDC process step is sufficient to produce high purity 1,3 butadiene.

For the extractive distillation process illustrated in FIG. 3, the selective solvent for the EDC include, for example, DMF, ACN, NMP, DMAC, furfural, phenol, sulfolane, MEK, and mixtures thereof. Water can be included as the co-solvent. A prefer solvent is aqueous ACN or aqueous NMP. The EDC of FIG. 3 preferably has 150 to 250 trays.

EXAMPLES

The following examples are presented to further illustrate different aspects and embodiments of the invention and are not to be considered as limiting the scope of the invention.

Data in these examples were generated with computer simulation modeling of extractive distillation processes for recovering butadiene using representative commercial data.

Example 1

Comparative—Base Case

In this base case representing the ED process as illustrated in FIG. 1, the first EDC is operated under a reflux-to-distillate weight ratio (R/D) of 1.8 and the second EDC is operated under an R/D of 1.1. The solvent-to-hydrocarbon weight ratio (S/F) for the first EDC is 5.7 and for the second EDC is 1.7. This base case yields a purified butadiene product containing 99.85 wt % 1,3 butadiene with 98.5 wt % recovery, operated under a throughput of 58,000 to 59,000 Kg/Hr of $C_4$ hydrocarbon feed containing approximately 45 wt % 1,3 butadiene.

Referring to FIG. 1, from the feed tank 101, 58,800 Kg/Hr of a $C_4$ hydrocarbon fraction containing butadienes is fed continuously to the middle portion of the first EDC 102 at 49° C. and 4.6 Kg/cm² (pressure) via line 1. This stream contains approximately 46 wt % 1,3 butadiene, 14 wt % 1-butane, 24 wt % isobutene, 10 wt % 2-butenes, 5 wt % butanes, and 1 wt % acetylenes (mostly vinylacetylene). 336,000 Kg/Hr of DMF solvent containing 96 wt % DMF and 4 wt % squalane (tar) at 38° C. and 5.1 Kg/cm² is introduced to the upper portion of the first EDC 102 via line 2. In column 102 the DMF solvent contacts the rising hydrocarbon vapor and preferentially extracts the more polar components consisting of butadienes, and acetylenes, allowing vapor of the less polar components consisting of butenes and butanes to rise to the top of the column. The overhead vapor is then condensed before entering the accumulator where a major portion of the condensate is recycled to the top of column 102 as reflux at a reflux ratio of 1.8. The balance is withdrawn from line 6 as the raffinate product at 39° C. and 3.4 Kg/cm².

Rich solvent is transferred from the bottom of column 102 and fed to the first stripping column 103 via line 4 at 130° C. and 5.1 Kg/cm². Overhead vapor from column 103 containing approximately 85 wt % 1,3 butadiene, 2 wt % 1,2 butadiene, 3 wt % acetylenes (mostly vinylacetylene), 2 wt % cis-2-butene, and 7 wt % DMF solvent, is fed to compressor 108 via line 7 and the compressed mixture is then introduced into the middle portion of the second EDC 104 at 108° C. and 3.6 Kg/cm² via line 11. Lean solvent from the bottom of column 103 is fed to an upper portion of column 102 as the lean solvent feed via lines 8 and 2. A slip stream is withdrawn from line 8 and fed to solvent purification unit 109 via line 9 for solvent regeneration and regenerated lean solvent is recycled via line 10 and mixed with the lean solvent in line 8. Lean DMF solvent containing 96 wt % DMF and 4 wt % squalane is fed to the upper portion of column 104 via line 12 at 38° C. and 3.0 Kg/cm². The raffinate stream exiting the top of column 104 via line 13 is condensed through cooler C2 and collected in accumulator A2, where a larger portion of the condensate is recycled via line 14 to the top of column 104 as reflux at a reflux ratio of 1.1. The smaller portion of the condensate containing approximately 97 wt % 1,3 butadiene, 3 wt % cis-2-butene and trace of methylacetylene is transferred via line 15 to the acetylene fractionator 106 at 37° C. and 3.0 Kg/cm².

Rich solvent consists of 89 wt % DMF, 3.5 wt % squalane, 1.4 wt % vinylacetylene, and 0.35 wt % ethylacetylene, is withdrawn from the bottom of column 104 and then fed to the second stripping column 105 via line 16. The stripped acetylene mixtures are removed from the overhead of column 105 via line 17, which is condensed through cooler C3 and collected in accumulator A3. A portion of the condensate is recycled as the reflux via line 18 and the other portion is purged as fuel via lines 19 and 27. Lean solvent from the bottom of column 105 is recycled to ED column 104 through lines 20, 21, and 12. A slip stream is withdrawn from line 20 and fed to solvent purification unit 109 via line 22 for solvent regeneration and regenerated lean solvent is recycled via line 23 and mixed with the lean solvent in line 21.

The overhead from column 106 is condensed in cooler C4 and collected in accumulator A4 through line 24, where a portion of the condensate is recycled as the reflux via line 25 and the other portion is removed via line 26 and combined with line 19. The combined mixture containing approximately 90 wt % vinylacetylene, 8.8 wt % butadiene and 1.2 wt % methylacetylene is then purged through line 27 at rate of about 1,000 Kg/Hr. The bottom stream from column 106 is transferred via line 28 to feed the butadiene fractionator 107. Purified butadiene exiting the top of column 107 via line 30 is condensed in cooler C5 and collected in accumulator A5, where a portion is recycled as reflux via line 31 and the balance is withdrawn through line 32 as the purified butadiene product which comprises 99.85 wt % 1,3 butadiene and 0.14 wt % cis-2-butene at rate of 27,000 Kg/Hr. The bottom of column 107 consists of 70 wt % cis-2-butene, 20 wt % 1,3 butadiene, and 10 wt % 1,2 butadiene, is purged via line 29 as fuel at a rate of approximately 1,000 Kg/Hr.

Data for the key process streams of this base case including the stream composition, flow rate, temperature and pressure are summarized in Table 1.

TABLE 1

Composition of Process Streams of the Base Case (wt %)

| Stream No. | 1 | 2 | 6 | 11 | 12 | 15 | 16 | 27 | 29 | 30 |
|---|---|---|---|---|---|---|---|---|---|---|
| Butanes | 4.7 | 0 | 9.2 | 0 | 0 | 0 | 0 | 0 | 0 | 0 |
| 1-Butene | 14.4 | 0 | 27.9 | 0 | 0 | 0 | 0 | 0 | 0 | 0 |
| i-Butene | 23.5 | 0 | 45.7 | 0 | 0 | 0 | 0 | 0 | 0 | 0 |
| 2-Butenes | 10.0 | 0 | 16.9 | 2.2 | 0 | 2.6 | 0.1 | 0 | 69.5 | 0.1 |
| 1,3 Butadiene | 45.9 | 0 | 0.2 | 85.2 | 0 | 97.0 | 4.7 | 8.8 | 21.0 | 99.9 |
| 1,2 Butadiene | 0.4 | 0 | 0 | 2.2 | 0 | 0.4 | 1.0 | 0 | 9.7 | 0 |
| Methylacetylene | 0.02 | 0 | 0 | 0.04 | 0 | 0.04 | 0 | 1.2 | 0 | 0 |
| Ethylacetylene | 0.2 | 0 | 0 | 0.7 | 0 | 0 | 0.3 | 0 | 0 | 0 |
| Vinylacetylene | 0.9 | 0 | 0 | 2.7 | 0 | 0 | 1.4 | 90.0 | 0 | 0 |
| Squalane (Tar) | 0 | 4.0 | 0 | 0 | 4.0 | 0 | 3.5 | 0 | 0 | 0 |
| DMF | 0 | 96.0 | 0 | 6.8 | 96.0 | 0 | 88.8 | 0 | 0 | 0 |
| Rate (Kg/Hr)/$10^3$ | 58.8 | 336 | 30.3 | 35.4 | 60.5 | 27.7 | 68.1 | 1.0 | 1.0 | 26.6 |
| Temp (° C.) | 49 | 38 | 39 | 108 | 38 | 37 | 130 | 43 | 58 | 42 |
| Press (Kg/cm$^2$) | 4.6 | 5.1 | 3.4 | 3.6 | 3.1 | 3.1 | 3.6 | 4.4 | 4.4 | 3.8 |

In this base case, the energy requirements for the first EDC are estimated to be $6.638 \times 10^6$ Kcal/Hr for cooling and condensing, and $23.600 \times 10^6$ Kcal/Hr for heating at the reboiler, so the total is $30.238 \times 10^6$ Kcal/Hr. Likewise, total energy requirements for the second EDC are estimated at $9.385 \times 10^6$ Kcal/Hr which includes $4.973 \times 10^6$ Kcal/Hr for cooling and condensing, and $4.412 \times 10^6$ Kcal/Hr for reboiler heating.

Example 2

Significant Reduced Reflux at the First and Second EDCs

This example demonstrates that the performances of the first and second EDCs are not affected by substantially reducing the column overhead reflux and the energy consumption of these two EDCs is significantly decreased as a result of the diminished reflux.

Referring to FIG. 2, the same C$_4$ hydrocarbon fraction containing approximately 46 wt % butadiene is fed continuously to the middle portion of the first EDC 202 at the same flow rate via line 41, under the same temperature and pressure as those of the base case in Example 1. The same DMF solvent containing 96 wt % DMF and 4 wt % squalane (tar) is introduced to the upper portion of the first EDC 202 via line 42, under the same temperature and pressure as the base case. The overhead vapor in line 43 is then condensed by cooler C6 and collected in the accumulator A6 where only a very minor portion of the condensate is recycled to the top of column 202 as reflux at a reflux ratio of 0.18 via line 45A (about 10% of the reflux ratio in base case). The balance is withdrawn from line 45 as a raffinate product that has a composition substantially that is the same as that of the base case (Stream 6 in Table 1). This result indicates that the performance of the first EDC 202 is essentially unaffected by a 90% reduction in the overhead reflux. To eliminate entrained solvent in the raffinate product, the solvent feed tray is moved from tray 10 to tray 30, and the hydrocarbon feed tray is moved from tray 136 to 150 (counting from the top of the first EDC 202).

Rich solvent is transferred from the bottom of first EDC 202 and is fed to the first stripping column 203 via line 44 at 130° C. and 5.1 Kg/cm$^2$. Overhead vapor from column 203 is fed to compressor 208 via line 46 and the compressed mixture is then introduced into the middle portion of the second EDC 204 at 108° C. and 3.6 Kg/cm$^2$ via line 50. Lean DMF solvent having the same composition as the stream in line 42 is fed to the upper portion of EDC 204 via line 51 at 38° C. and 3.0 Kg/cm$^2$. The raffinate stream exiting the top of second EDC 204 via line 52 is condensed through cooler C7 and collected in accumulator A7, where a small portion of the condensate is recycled via line 53A to the top of second EDC 204 as reflux at a reflux ratio of 0.3 (compared to 1.1 for the base case). The other portion of the condensate is transferred via line 53 to the acetylene fractionator 206 at 37° C. and 3.0 Kg/cm$^2$. The composition of line 53 is substantially the same as that of the base case (Stream 15 in Table 1), except the stream contains 60 ppm ethylacetylene and 40 ppm vinylacetylene. The ethylacetylene and vinylacetylene impurities can be substantially removed in butadiene fractionator 207. The solvent feed tray (at tray 11 counting from the top of column 204) and the hydrocarbon feed tray (at tray 57) are not changed, since no entrained solvent is detected in the raffinate stream 53.

Rich solvent withdrawn from the bottom of second EDC 204 is then fed to the second stripping column 205 via line 54. The stripped acetylene mixture (mainly vinylacetylene) is removed from the overhead of column 205 via line 55, which is condensed through cooler C8 and collected in accumulator A8. A portion of the condensate is recycled as the reflux via line 56 and the other portion is purged as fuel via lines 57 and 65. Lean solvent from the bottom of column 205 is recycled to second EDC 204 through lines 58, 59, and 51. A slip stream is withdrawn from line 58 and fed to solvent purification unit 209 via line 60 for solvent regeneration.

The overhead from column 206 is condensed in cooler C9 and collected in accumulator A9 through line 62, where a portion of the condensate is recycled as the reflux via line 63 and the other portion is removed via line 64 and combined with line 57. The combined mixture containing approximately 89 wt % vinylacetylene, 9.4 wt % butadiene and 1.2 wt % methylacetylene is then purged through line 65 at rate of about 1,000 Kg/Hr. The bottom stream from column 206 is transferred via line 66 to feed the butadiene fractionator 207. Purified butadiene exiting the top of column 207 via line 68 is condensed in cooler C10 and collected in accumulator A10, where a portion is recycled as reflux via line 69 and the balance is withdrawn through line 70 as the purified butadiene product which comprises 99.85 wt % 1,3 butadiene, 0.13 wt % cis-2-butene and free of acetylenes at rate of 26,800 Kg/Hr. The bottom of column 207 consists of 67 wt % cis-2-butene, 11 wt % 1,3 butadiene, and 19 wt % 1,2 butadiene, 1.6 wt % ethylacetylene, and 1.1 wt % vinylacetylene is purged via line 67 as fuel at a rate of approximately 1,000 Kg/Hr.

Data for the key process streams of this "low reflux" case as shown in FIG. 2, including the stream composition, flow rate, temperature and pressure are summarized in Table 2.

For this "low reflux" case, the energy requirements for the first EDC are estimated to be $2.665 \times 10^6$ Kcal/Hr for cooling and condensing (59.9% reduction from the base case), and $19.590 \times 10^6$ Kcal/Hr for heating at the reboiler (13.9% reduction), so the total is $22.255 \times 10^6$ Kcal/Hr (26.4% reduction). Again, in this "low reflux" case, total energy requirements for the second EDC are estimated at $5.871 \times 10^6$ Kcal/Hr (37.4% reduction from the base case), in which, $4.973 \times 10^6$ Kcal/Hr for cooling and condensing (37.8% reduction), and $2.776 \times 10^6$ Kcal/Hr for reboiler heating (37.1% reduction).

Example 3

The Optimum Reflux at the First EDC

Examples 1 and 2 demonstrate that the first EDC consumes three times the energy as the second EDC. This example shows a method of determining an optimal reflux to generate the maximum energy savings in the first EDC without affecting its performance. Table 3 summarizes the key stream compositions of the first EDC for the base case as well as for two other cases operating under different reflux ratios. Table 3 also compares the energy requirements of the first EDC under different reflux ratios.

TABLE 2

Composition of Process Streams of the Case with Substantially Reduced Reflux in the first & second EDC (wt %)

| Stream No. | 41 | 42 | 45 | 50 | 51 | 53 | 54 | 65 | 67 | 70 |
|---|---|---|---|---|---|---|---|---|---|---|
| Butanes | 4.7 | 0 | 9.2 | 0 | 0 | 0 | 0 | 0 | 0 | 0 |
| 1-Butene | 14.4 | 0 | 27.9 | 0 | 0 | 0 | 0 | 0 | 0 | 0 |
| i-Butene | 23.5 | 0 | 45.7 | 0 | 0 | 0 | 0 | 0 | 0 | 0 |
| 2-Butenes | 10.0 | 0 | 17.0 | 2.1 | 0 | 2.5 | 0 | 0 | 67.0 | 0.1 |
| 1,3 Butadiene | 45.9 | 0 | 0.1 | 86.6 | 0 | 96.6 | 4.8 | 9.4 | 11.0 | 99.9 |
| 1,2 Butadiene | 0.4 | 0 | 0 | 0.9 | 0 | 0.7 | 0.2 | 0 | 19.2 | 0 |
| Methylacetylene | 0.02 | 0 | 0 | 0.04 | 0 | 0.04 | 0 | 1.2 | 0 | 0 |
| Ethylacetylene | 0.2 | 0 | 0 | 0.6 | 0 | 0.06 | 0.3 | 0 | 1.6 | 3 (ppm) |
| Vinylacetylene | 0.9 | 0 | 0 | 2.6 | 0 | 0.04 | 1.3 | 89.3 | 1.1 | 1 (ppm) |
| Squalane (Tar) | 0 | 4.0 | 0 | 0 | 4.0 | 0 | 3.6 | 0 | 0 | 0 |
| DMF | 0 | 96.0 | 0 | 7.0 | 96.0 | 0 | 89.7 | 0 | 0 | 0 |
| Rate (Kg/Hr)/$10^3$ | 58.8 | 336 | 30.3 | 34.8 | 60.5 | 27.9 | 67.4 | 1.1 | 1.0 | 26.8 |
| Temp (° C.) | 49 | 38 | 39 | 108 | 38 | 37 | 130 | 43 | 58 | 42 |
| Press (Kg/cm$^2$) | 4.6 | 5.1 | 3.4 | 3.6 | 3.1 | 3.1 | 3.6 | 4.4 | 4.4 | 3.8 |

TABLE 3

Key Stream Composition and Energy Consumption
of the First EDC under Various Reflux Ratios

| Reflux Ratio | | | 1.8 (Base Case) | | 0.09 (5%) | | 0.00 (No Reflux) | |
|---|---|---|---|---|---|---|---|---|
| Stream No. | 41 | 42 | 44 | 45 | 44 | 45 | 44 | 45 |
| Butanes | 4.7 | 0 | 0 | 9.2 | 0 | 9.2 | 0 | 9.2 |
| 1-Butene | 14.4 | 0 | 0 | 27.9 | 0 | 27.9 | 0 | 27.9 |
| i-Butene | 23.5 | 0 | 0 | 45.7 | 0 | 45.7 | 0 | 45.7 |
| 2-Butenes | 10.0 | 0 | 0.2 | 16.9 | 0.2 | 17.0 | 0.2 | 16.7 |
| 1,3 Butadiene | 45.9 | 0 | 8.4 | 0.2 | 8.4 | 0.1 | 8.5 | 0 |
| 1,2 Butadiene | 0.4 | 0 | 0.1 | 0 | 0.1 | 0 | 0.1 | 0 |
| Methylacetylene | 200 ppm | 0 | 37 ppm | 1 ppm | 38 ppm | 0 | 38 ppm | 0 |
| Ethylacetylene | 1900 ppm | 0 | 581 ppm | 0 | 547 ppm | 0 | 547 ppm | 0 |
| Vinylacetylene | 8600 ppm | 0 | 2515 ppm | 0 | 2486 ppm | 0 | 2486 ppm | 0 |
| Squalane (Tar) | 0 | 4.0 | 3.6 | 0 | 3.6 | 0 | 3.6 | 0 |
| DMF | 0 | 96.0 | 87.3 | 0 | 87.3 | 0 | 87.3 | 486 ppm |
| Reflux Rate (Kg/Hr) | | | 53,000 | | 2,700 | | 0 | |
| Condenser Duty (Kcal/Hr) × $10^6$ | | | 6.638 | | 2.618 | | 2.525 | |
| Reboiler Duty (Kcal/Hr) × $10^6$ | | | 23.600 | | 15.113 | | 14.937 | |
| Energy Savings | | | | | | | | |
| Condenser | | | (Base) | | 60.6% | | 62.0% | |
| Reboiler | | | (Base) | | 36.0% | | 36.7% | |
| Total | | | (Base) | | 41.4% | | 42.3% | |

The information confirms that the separation performance of the first EDC is not affected by the reduction in the overhead reflux even when reduced by as much as 95% or even 100% (no reflux). The total energy savings for the 95% reduction in reflux process is found to be 41.4%, which is significantly higher than the 26.4% savings achieved by the 90% reduction in reflux. However, the difference in energy savings between 95% reduction and 100% reduction in reflux (that is, no reflux) is quite insignificant as shown in table 3.

It should be noted that, under no reflux, the entrained solvent in the raffinate stream is around 500 ppm, an amount that cannot be ignored. For non-aqueous solvents, such as DMF, the reflux can be reduced between 95 and 100% as long as no entrained solvent is detected in the overhead raffinate product. For aqueous solvents, such as aqueous ACN, or aqueous NMP, the EDC can be operated under no reflux, but the raffinate product needs to be washed with water in a separated wash tank or column, where the washed water can be recycled to the existing water system for the solvent and water recovery.

With substantially reduced reflux in the existing EDC, one would expect that the process throughput could be increased proportionally to the rate of reduction of the reflux, if either the first or the second EDC is the bottleneck of the process.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. An extractive distillation (ED) process, that employs a first extractive distillation column (EDC) and a second EDC for recovering high purity 1,3 butadiene from $C_4$ hydrocarbon fractions, that comprises the steps of:

(a) introducing a $C_4$ hydrocarbon feed mixture containing 1,3 butadiene into a middle portion of a first EDC and introducing a first non-aqueous solvent-rich stream into an upper portion of the first EDC as a first selective non-aqueous solvent feed;

(b) recovering a first raffinate stream rich in less polar hydrocarbon components from a top of the first EDC, that is substantially free of 1,3 butadiene and the first selective non-aqueous solvent, and withdrawing a second non-aqueous solvent-rich stream containing the first selective non-aqueous solvent and more polar components from a bottom of the first EDC;

(c) introducing the second non-aqueous solvent-rich stream into a middle portion of a first stripping column (SC), recovering a more polar hydrocarbon-rich stream from a top of the SC, which is then fed to a compressor to yield a compressed stream, and removing a third non-aqueous solvent-rich stream from a bottom of that SC, that is recycled to the upper portion of the first EDC as the first selective non-aqueous solvent feed;

(d) introducing the compressed stream in step (c) into a middle portion of a second EDC and introducing a fourth non-aqueous solvent-rich stream into an upper portion of the second EDC as a second selective non-aqueous solvent feed;

(e) recovering a second raffinate stream containing essentially 1,3 butadiene with minor amounts of butenes, traces of acetylenes, and substantially free of the second selective non-aqueous solvent from a top of the second EDC, and withdrawing a fifth non-aqueous solvent-rich stream from a bottom of the second EDC;

(f) introducing the fifth non-aqueous solvent-rich stream into a middle portion of a second stripping column (SC), removing a stream rich in vinylacetylene from a top of the second SC and recovering a sixth non-aqueous solvent-rich stream from a bottom of the second SC, that is recycled to the upper portion of the second EDC as the second selective non-aqueous solvent feed;

(g) introducing the second raffinate stream from step (e) into a middle portion of an acetylene fractionator, removing a small stream rich in 1,3 butadiene and methylacetylene from a top and recovering a crude 1,3 butadiene stream from a bottom of the fractionator; and (h) introducing the crude 1,3 butadiene stream from step (g) into a middle portion of a butadiene fractionator, where the purified 1,3 butadiene is recovered from an overhead and minor amounts of impurities are purged from a bottom of the fractionator wherein the first EDC and the second EDC are each operated under a reduced reflux-to-distillate ratio with a reflux-to-distillate ratio in the range of greater than 0 to 1 and with the proviso that the purity of the first raffinate stream with respect to 1,3 butadiene is substantially the same as that of the first raffinate steam when the first EDC operates at a reflux-to-distillate ratio of between 2 to 3 and the second EDC operates at a reflux-to-distillate ratio of greater than 1.

2. The process of claim 1 wherein the first EDC is operated under a reflux-to-distillate ratio of up to 1.0 and the second EDC is operated under a reflux-to-distillate ratio of up to 0.7.

3. The process of claim 2 wherein the first EDC is operated under a reflux-to-distillate ratio of up to 0.36 and the second EDC is operated under a reflux-to-distillate ratio of up to 0.33.

4. The process of claim 1 wherein the more polar hydrocarbons comprise butadienes and acetylenes and the less polar hydrocarbons comprise butanes and butenes.

5. The process of claim 1 wherein each of the first selective non-aqueous solvent and second selective non-aqueous solvent is selected from the group consisting of dimethylformamide (DMF), acetonitrile (ACN), N-methyl-pyrrolidone (NMP), dimethylacetamide (DMAC), furfural, phenol, sulfolane, methylethylketone (MEK), and mixtures thereof.

6. The process of claim 1 wherein the first EDC comprises 150 to 250 trays and the second EDC comprises 60 to 120 trays.

7. The process of claim 1 wherein the first selective non-aqueous solvent enters through an entry point of the first EDC that is adjusted downward 12 to 60 trays away from the top of the column to prevent entrained non-aqueous solvent from the overhead raffinate streams of the first EDC and the hydrocarbon feed enters through an entry point of the first EDC that is adjusted downward 110 to 180 trays from the top to maintain the performance of the first EDC.

8. An extractive distillation (ED) process, that employs a single wash section and a single distillation column that functions as an extractive distillation column (EDC), using an aqueous selective solvent, for recovering high purity 1,3 butadiene from $C_4$ hydrocarbon fractions, which comprises the steps of:
  (a) introducing a $C_4$ hydrocarbon feed mixture containing 1,3 butadiene into a middle portion of the EDC and introducing a first solvent-rich stream into an upper portion of the EDC as a selective solvent feed wherein the EDC is operated under a reflux-to-distillation ratio in the range of greater than 0 to 1;
  (b) recovering a first raffinate stream rich in less polar hydrocarbon components from a top of the EDC, that contains mainly butenes and lesser amounts of butanes and that is substantially free of 1,3 butadiene, and withdrawing a second solvent-rich stream containing the selective solvent and more polar components from a bottom of the EDC, wherein the more polar components comprise butadienes and acetylenes, with the proviso that the purity of the first raffinate stream with respect to 1,3 butadiene is substantially the same as that of the first raffinate steam when the EDC operates at a reflux-to-distillate ratio of between 2 to 3;
  (c) introducing the second solvent-rich stream into a flash drum and recovering butadiene-rich vapor in a top of the flash drum and recovering rich solvent that is partially depleted of butadiene in a bottom of the flash drum;
  (d) introducing the rich solvent recovered in step (c) to an upper portion of a first stripping column, introducing lean solvent from a bottom of the second stripping into the upper portion of the first stripping column, withdrawing a stream rich in acetylenes from a side-cut of the first stripping column for proper disposal, recovering a butadiene-rich vapor containing heavier impurities from the top of the first stripping column, and recovering the lean solvent from the bottom of first stripping column, which is recycled back to the upper portion of the EDC in step (a);
  (e) combining the butadiene-rich vapor stream from the top of the first stripping column in step (d) and the butadiene-rich vapor stream from the top of the flash drum to form a combined mixture rich in 1,3 butadiene that is fed to a compressor;
  (f) splitting the compressed vapor from step (e) into three portions: (i) a first major portion for recycling to the lower portion of the EDC for improving its operation; (ii) a second major portion for recycling to middle portion of the second stripping column for recovering purified 1,3 butadiene product; and (iii) a minor portion to the single water wash section for removing and recovering $C_5$ hydrocarbons; and
  (g) introducing the first raffinate stream from step (b) to the water wash of section (f) to remove entrained solvent from the first raffinate stream.

9. The process of claim 8 wherein the EDC is operated under a reflux-to-distillation ratio of up to 0.18.

10. The process of claim 8 wherein the EDC is operated under a reflux-to-distillation ratio of up to 0.36.

11. The process of claim 8 wherein the aqueous selective solvent for the EDC is selected from the group consisting of acetonitrile (ACN), N-methyl-pyrrolidone (NMP), dimethylacetamide (DMAC), furfural, phenol, sulfolane, methylethylketone (MEK), and mixtures thereof.

12. The process of claim 11 wherein the aqueous selective solvent comprises aqueous ACN.

13. The process of claim 11 wherein the aqueous selective solvent comprises aqueous NMP.

14. The process of claim 8 wherein the EDC comprises 150 to 250 trays.

15. An extractive distillation (ED) process, that employs a first extractive distillation column (EDC) and a second EDC for recovering high purity 1,3 butadiene from $C_4$ hydrocarbon fractions, that comprises the steps of:
  (a) introducing a $C_4$ hydrocarbon feed mixture containing 1,3 butadiene into a middle portion of a first EDC and introducing a first aqueous solvent-rich stream into an upper portion of the first EDC as a first selective aqueous solvent feed;
  (b) recovering a first raffinate stream rich in less polar hydrocarbon components from a top of the first EDC, that is substantially free of 1,3 butadiene and the first selective aqueous solvent, and withdrawing a second aqueous solvent-rich stream containing the first selective aqueous solvent and more polar components from a bottom of the first EDC;
  (c) introducing the second aqueous solvent-rich stream into a middle portion of a first stripping column (SC), recovering a more polar hydrocarbon-rich stream from a top of the SC, which is then fed to a compressor to yield a compressed stream, and removing a third aqueous solvent-rich stream from a bottom of that SC, that is recycled to the upper portion of the first EDC as the first selective aqueous solvent feed;

(d) introducing the compressed stream in step (c) into a middle portion of a second EDC and introducing a fourth aqueous solvent-rich stream into an upper portion of the second EDC as a second selective aqueous solvent feed;

(e) recovering a second raffinate stream containing essentially 1,3 butadiene with minor amounts of butenes, traces of acetylenes, and substantially free of the second selective aqueous solvent from a top of the second EDC, and withdrawing a fifth aqueous solvent-rich stream from a bottom of the second EDC;

(f) introducing the fifth aqueous solvent-rich stream into a middle portion of a second stripping column (SC), removing a stream rich in vinylacetylene from a top of the second SC and recovering a sixth aqueous solvent-rich stream from a bottom of the second SC, that is recycled to the upper portion of the second EDC as the second selective aqueous solvent feed;

(g) introducing the second raffinate stream from step (e) into a middle portion of an acetylene fractionator, removing a small stream rich in 1,3 butadiene and methylacetylene from a top and recovering a crude 1,3 butadiene stream from a bottom of the fractionator; and (h) introducing the crude 1,3 butadiene stream from step (g) into a middle portion of a butadiene fractionator, where the purified 1,3 butadiene is recovered from an overhead and minor amounts of impurities are purged from a bottom of the fractionator wherein the overhead raffinate stream from the first EDC is washed with water to remove entrained aqueous solvent without adjusting solvent and hydrocarbon feed entry points in the first EDC wherein the first EDC and the second EDC are each operated under a reduced reflux-to-distillate ratio with a reflux-to-distillate ratio in the range of greater than 0 to 1 and with the proviso that the purity of the first raffinate stream with respect to 1,3 butadiene is substantially the same as that of the first raffinate steam when the first EDC operates at a reflux-to-distillate ratio of between 2 to 3 and the second EDC operates at a reflux-to-distillate ratio of greater than 1.

16. The process of claim 15 wherein the first EDC is operated under a reflux-to-distillate ratio of up to 1.0 and the second EDC is operated under a reflux-to-distillate ratio of up to 0.7.

17. The process of claim 16 wherein the first EDC is operated under a reflux-to-distillate ratio of up to 0.36 and the second EDC is operated under a reflux-to-distillate ratio of up to 0.33.

18. The process of claim 15 wherein each of the first selective aqueous solvent and second selective aqueous solvent is selected from the group consisting of acetonitrile (ACN), N-methyl-pyrrolidone (NMP), furfural, phenol, sulfolane, methylethylketone (MEK), and mixtures thereof and wherein the each of the first selective aqueous solvent and second selective aqueous solvent includes water as a co-solvent.

19. The process of claim 15 wherein the first EDC comprises 150 to 250 trays and the second EDC comprises 60 to 120 trays.

\* \* \* \* \*